(12) United States Patent
McDonald et al.

(10) Patent No.: US 8,483,844 B2
(45) Date of Patent: Jul. 9, 2013

(54) ELECTRICAL STIMULATION LEADS HAVING RF COMPATIBILITY AND METHODS OF USE AND MANUFACTURE

(71) Applicant: Boston Scientific Neuromodulation Corporation, Valencia, CA (US)

(72) Inventors: Matthew Lee McDonald, Pasadena, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/728,579

(22) Filed: Dec. 27, 2012

(65) Prior Publication Data

US 2013/0138181 A1 May 30, 2013

Related U.S. Application Data

(62) Division of application No. 12/238,039, filed on Sep. 25, 2008, now Pat. No. 8,364,279.

(51) Int. Cl.
*A61N 1/00* (2006.01)

(52) U.S. Cl.
USPC ........................................................ 607/116

(58) Field of Classification Search
USPC ............................ 607/116–138; 600/373–381
See application file for complete search history.

(56) References Cited

U.S. PATENT DOCUMENTS

| | | | |
|---|---|---|---|
| 4,044,775 A | 8/1977 | McNichols | |
| 4,122,854 A | 10/1978 | Blackett | |
| 4,167,190 A | 9/1979 | Sorenson et al. | |
| 4,237,887 A | 12/1980 | Gonser | |
| 5,014,705 A | 5/1991 | Graupe et al. | |
| 5,022,404 A | 6/1991 | Hafner | |
| 5,296,813 A | 3/1994 | Holmes et al. | |
| 5,405,363 A | 4/1995 | Kroll et al. | |
| 5,443,470 A | 8/1995 | Stern et al. | |
| 5,694,940 A | 12/1997 | Unger et al. | |

(Continued)

FOREIGN PATENT DOCUMENTS

| WO | WO-88/09152 A1 | 12/1988 |
|---|---|---|
| WO | WO-94/23794 A1 | 10/1994 |

(Continued)

OTHER PUBLICATIONS

U.S. Appl. No. 11/965,627, filed Dec. 27, 2007.

(Continued)

*Primary Examiner* — Mark W Bockelman
(74) *Attorney, Agent, or Firm* — Frommer Lawrence & Haug LLP; Bruce E. Black

(57) ABSTRACT

A neurostimulation lead or lead extension includes a lead body having a proximal end and a distal end. A plurality of first contacts are disposed on the distal end of the lead body. A plurality of second contacts are disposed on a proximal end of the lead body. A plurality of conductors extend along the lead body. Each of the plurality of conductors electrically couples at least one of the first contacts to at least one of the second contacts. At least one of the conductors includes at least one switch disposed along a length of the conductor. The at least one switch is configured and arranged to separate the conductor into a plurality of individual segments when the at least one switch is opened.

20 Claims, 7 Drawing Sheets

U.S. PATENT DOCUMENTS

| | | | |
|---|---|---|---|
| 5,699,801 A | 12/1997 | Atalar et al. |
| 5,928,145 A | 7/1999 | Ocali et al. |
| 6,031,375 A | 2/2000 | Atalar et al. |
| 6,041,260 A | 3/2000 | Stern et al. |
| 6,181,969 B1 | 1/2001 | Gord |
| 6,233,488 B1 | 5/2001 | Hess |
| 6,263,229 B1 | 7/2001 | Atalar et al. |
| 6,408,202 B1 | 6/2002 | Lima et al. |
| 6,516,227 B1 | 2/2003 | Meadows et al. |
| 6,549,800 B1 | 4/2003 | Atalar et al. |
| 6,606,513 B2 | 8/2003 | Lardo et al. |
| 6,609,029 B1 | 8/2003 | Mann et al. |
| 6,609,032 B1 | 8/2003 | Woods et al. |
| 6,628,980 B2 | 9/2003 | Atalar et al. |
| 6,675,033 B1 | 1/2004 | Lardo et al. |
| 6,701,176 B1 | 3/2004 | Halperin et al. |
| 6,714,809 B2 | 3/2004 | Lee et al. |
| 6,741,892 B1 | 5/2004 | Meadows et al. |
| 6,898,454 B2 | 5/2005 | Atalar et al. |
| 6,904,307 B2 | 6/2005 | Karmarkar et al. |
| 7,076,283 B2 | 7/2006 | Cho et al. |
| 7,096,068 B2 | 8/2006 | Mass et al. |
| 7,127,287 B2 | 10/2006 | Duncan et al. |
| 7,133,714 B2 | 11/2006 | Karmarkar et al. |
| 7,212,110 B1 | 5/2007 | Martin et |
| 7,236,816 B2 | 6/2007 | Kumar et al. |
| 7,244,150 B1 | 7/2007 | Brase et al. |
| 7,310,556 B2 | 12/2007 | Bulkes |
| 7,412,276 B2 | 8/2008 | Halperin et al. |
| 7,493,174 B2 | 2/2009 | Belalcazar et al. |
| 7,551,953 B2 | 6/2009 | Lardo et al. |
| 7,561,906 B2 | 7/2009 | Atalar et al. |
| 7,599,729 B2 | 10/2009 | Atalar et al. |
| 7,761,165 B1 | 7/2010 | He et al. |
| 7,778,682 B2 | 8/2010 | Kumar et al. |
| 7,822,460 B2 | 10/2010 | Halperin et al. |
| 7,844,319 B2 | 11/2010 | Susil et al. |
| 7,848,788 B2 | 12/2010 | Tulley et al. |
| 7,953,498 B1 | 5/2011 | Carbunaru et al. |
| 7,957,783 B2 | 6/2011 | Atalar et al. |
| 8,055,351 B2 | 11/2011 | Atalar et al. |
| 8,108,028 B2 | 1/2012 | Karmarkar |
| 8,260,434 B2 | 9/2012 | DiGiore et al. |
| 8,332,043 B1 | 12/2012 | Jaax et al. |
| 8,364,279 B2 * | 1/2013 | McDonald et al. | 607/116 |
| 2002/0072780 A1 | 6/2002 | Foley |
| 2003/0114905 A1 | 6/2003 | Kuzma |
| 2003/0135246 A1 | 7/2003 | Mass et al. |
| 2003/0139782 A1 | 7/2003 | Duncan et al. |
| 2003/0149456 A1 | 8/2003 | Rottenberg et al. |
| 2003/0233099 A1 | 12/2003 | Danaek et al. |
| 2004/0059392 A1 | 3/2004 | Parramon et al. |
| 2004/0162595 A1 | 8/2004 | Foley |
| 2004/0181177 A1 | 9/2004 | Lee et al. |
| 2005/0165465 A1 | 7/2005 | Pianca et al. |
| 2005/0187584 A1 | 8/2005 | Denker et al. |
| 2005/0245970 A1 | 11/2005 | Erickson et al. |
| 2005/0283202 A1 | 12/2005 | Gellman |
| 2006/0085049 A1 | 4/2006 | Cory et al. |
| 2006/0217767 A1 | 9/2006 | Bulkes |
| 2006/0259088 A1 | 11/2006 | Pastore et al. |
| 2007/0021814 A1 | 1/2007 | Inman et al. |
| 2007/0088416 A1 | 4/2007 | Atalar et al. |
| 2007/0150007 A1 | 6/2007 | Anderson et al. |
| 2007/0150036 A1 | 6/2007 | Anderson |
| 2007/0168004 A1 | 7/2007 | Walter |
| 2007/0219595 A1 | 9/2007 | He |
| 2007/0239243 A1 | 10/2007 | Moffitt et al. |
| 2007/0255332 A1 | 11/2007 | Cabelka et al. |
| 2008/0039709 A1 | 2/2008 | Karmarkar |
| 2008/0071320 A1 | 3/2008 | Brase |
| 2008/0243218 A1 | 10/2008 | Bottomley et al. |
| 2008/0262584 A1 | 10/2008 | Bottomley et al. |
| 2009/0198312 A1 | 8/2009 | Barker |
| 2009/0234368 A1 | 9/2009 | Gore |
| 2010/0076508 A1 | 3/2010 | McDonald et al. |
| 2011/0218422 A1 | 9/2011 | Atalar et al. |
| 2012/0071953 A1 | 3/2012 | Atalar et al. |

FOREIGN PATENT DOCUMENTS

| | | |
|---|---|---|
| WO | WO-96/00036 A1 | 1/1996 |
| WO | WO-98/48893 A1 | 11/1998 |
| WO | WO-98/48894 A1 | 11/1998 |
| WO | WO-99/55360 A1 | 11/1999 |
| WO | WO 02/09808 A1 | 2/2002 |
| WO | WO-02/26317 A1 | 4/2002 |
| WO | WO-03/061762 A1 | 7/2003 |
| WO | WO-03/066160 A1 | 8/2003 |
| WO | WO 03063946 A2 | 8/2003 |
| WO | WO-2006/009595 A1 | 1/2006 |
| WO | WO-2006/102187 A1 | 9/2006 |
| WO | WO-2006/115877 A1 | 11/2006 |
| WO | WO-2006/121424 A2 | 11/2006 |
| WO | WO-2007/013917 A1 | 2/2007 |
| WO | WO-2008/115426 A1 | 9/2008 |
| WO | WO-2008115383 A2 | 9/2008 |

OTHER PUBLICATIONS

U.S. Appl. No. 12/238,039, Official Communication mailed Jun. 20, 2012.

* cited by examiner

ELECTRICAL STIMULATION LEADS HAVING RF COMPATIBILITY AND METHODS OF USE AND MANUFACTURE

CROSS-REFERENCE TO RELATED APPLICATIONS

This patent application is a divisional of U.S. patent application Ser. No. 12/238,039 filed on Sep. 25, 2008, which is incorporated herein by reference.

FIELD

The present invention is directed to the area of implantable electrical stimulation systems and methods of making and using the systems. The present invention is also directed to implantable electrical stimulation leads having RF compatibility and implantable electrical stimulation systems that include the lead, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging (MRI) due to the large radio frequency (RF) pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, a neurostimulation lead or lead extension includes a lead body having a proximal end and a distal end. A plurality of first contacts are disposed on the distal end of the lead body. A plurality of second contacts are disposed on a proximal end of the lead body. A plurality of conductors extend along the lead body. Each of the plurality of conductors electrically couples at least one of the first contacts to at least one of the second contacts. At least one of the conductors includes at least one switch disposed along a length of the conductor. The at least one switch is configured and arranged to separate the conductor into a plurality of individual segments when the at least one switch is opened.

In another embodiment, a neurostimulation system includes a lead and a control module. The lead includes a lead body having a proximal end and a distal end. A plurality of first contacts are disposed on the distal end of the lead body. A plurality of second contacts are disposed on a proximal end of the load body. A plurality of conductors extend along the lead body. Each of the plurality of conductors electrically couples at least one of the first contacts to at least one of the second contacts. At least one of the conductors includes at least one switch disposed along a length of the conductor. The at least one switch is configured and arranged to separate the conductor into a plurality of individual segments when the at least one switch is opened. The control module is configured and arranged for coupling to the lead and to provide electrical stimulation signals to a patient through the electrodes of the lead.

In yet another embodiment, a method of neural stimulation includes implanting a lead in a patient. The lead includes a lead body having a proximal end and a distal end. A plurality of electrodes are disposed on the distal end of the lead body. A plurality of terminals are disposed on the proximal end of the lead body. A plurality of conductors extend along the lead body. Each of the plurality of conductors electrically couples at least one of the electrodes to at least one of the terminals. At least one of the conductors includes at least one switch disposed along a length of the conductor and is configured and arranged to separate the conductor into a plurality of individual segments when the at least one switch is opened. Signals are provided to the electrodes to produce neural stimulation of tissue in the patient. The at least one switch is opened when an intensity from at least one of a magnetic field or radio-frequency radiation meets a threshold criterion.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads and lead extensions having RF compatibility and implantable electrical stimulation systems that include the lead, as well as methods of making and using the leads and electrical stimulation systems.

Suitable implantable electrical stimulation systems include, but are not limited to, an electrode lead ("lead") with one or more electrodes disposed on a distal end of the lead and one or more contact terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; and 7,244,150; and U.S. patent application Ser. Nos. 10/353,101, 10/503,281, 11/238,240; 11/319,291; 11/375,638; 11/376,360; 11/393,991; 11/396,309; 11/565,547; 11/965,627; 12/018,397; 12/023,532; and 12/027,170 all of which are incorporated by reference.

Figure 1:
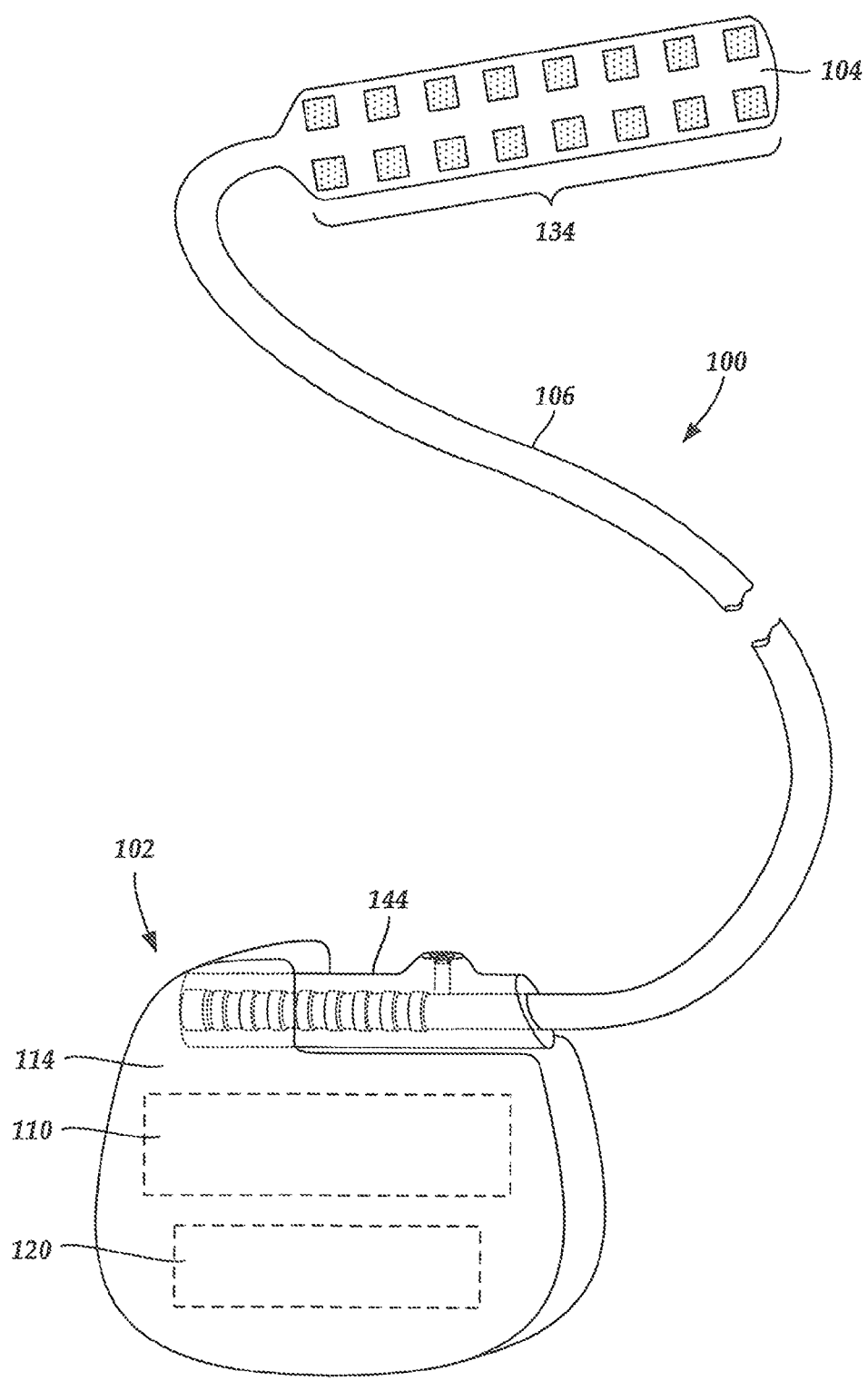
FIG. 1 is a schematic view of one embodiment of an electrical stimulation system, according to the invention.
Figure 2:
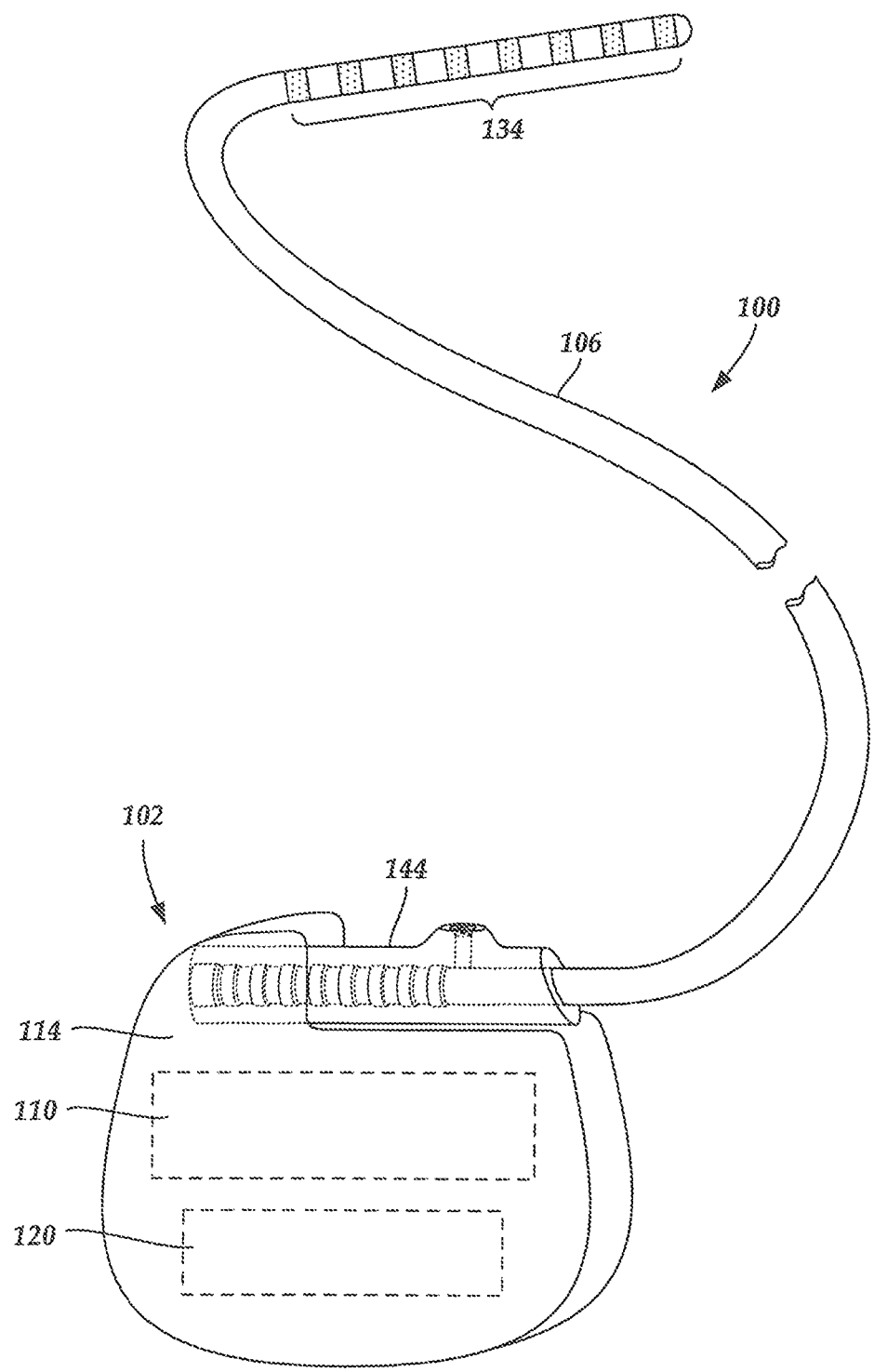
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 338 of FIG. 3B) into which the proximal end of the one or more lead bodies 106 can be plugged to make an electrical connection via conductive contacts on the control module 102 and terminals (e.g., 308 in FIGS. 3A and 322 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 308 in FIGS. 3A and 322 of FIG. 3B) are typically disposed at the proximal end of the one or more lead bodies 106 of the lead 100 for connection to corresponding conductive contacts (e.g., 302 in FIG. 3A) in the control module 102 (or to conductive contacts on a lead extension, an operating room cable, or an adaptor). Conductor wires (not shown) extend from the terminals (e.g., 308 in FIGS. 3A and 322 of FIG. 3B) to the electrodes 134. Typically, one or more electrodes 134 are electrically coupled to a terminal (e.g., 388 in FIGS. 3A and 322 of FIG. 3B). In some embodiments, each terminal (e.g., 308 in FIGS. 3A and 322 of FIG. 3B) is only connected to one electrode 134. There may also be one or more lumens (not shown) that open at, or near, the distal end of the lead, for example, for infusion of drugs or medication into the site of implantation of the paddle body 104.

Figure 3A:
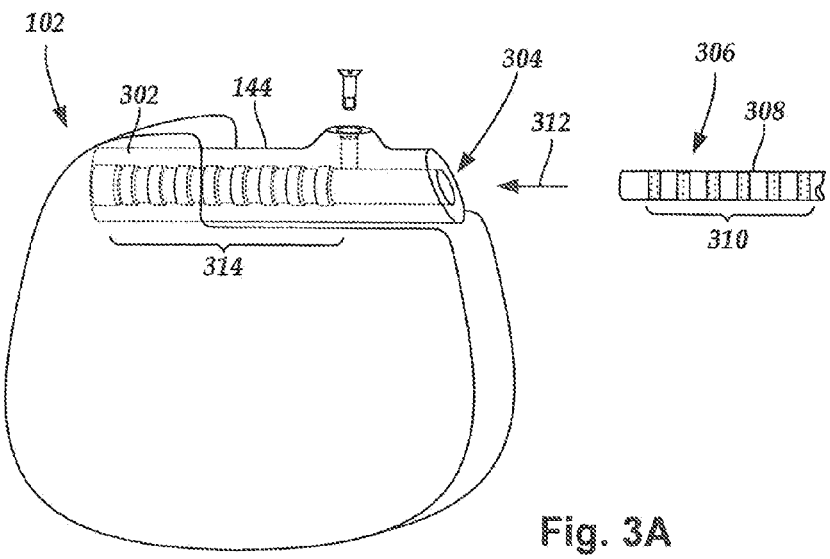
FIG. 3A is a schematic view of one embodiment of a proximal portion of a lead and a control module of an electrical stimulation system, according to the invention.

In at least some embodiments, leads are coupled to connectors disposed on control modules, in FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
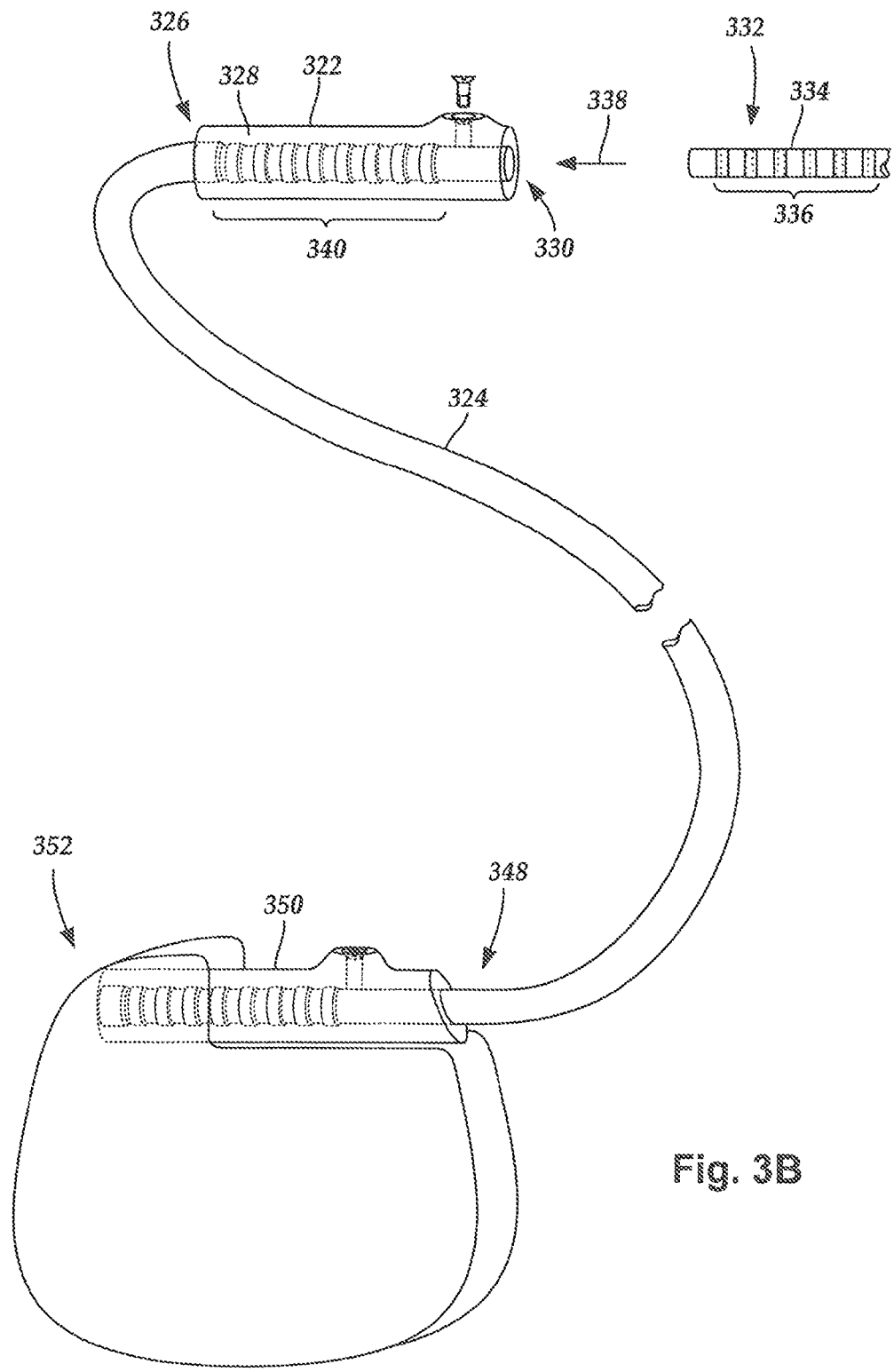
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326, in at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting contacts disposed on an elongated member (such as connecting an electrode to a terminal on a lead, or connecting a conductive contact to a terminal on a lead extension) can be arranged to eliminate or reduce the current generated in the conductor by RF irradiation, such as RF irradiation generated during magnetic resonance imaging (MRI). Reduction or elimination of the current can be accomplished using one or more switches with the conductor so that opening the switch(es) causes the conductor to be separated into multiple, unconnected segments. Such an arrangement is illustrated schematically in FIGS. 4A-4B.

Figure 4A:
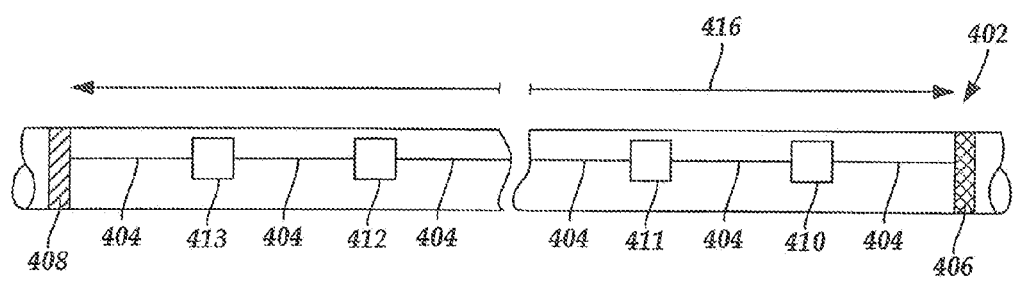
FIG. 4A is a schematic partial cross-sectional view of one embodiment of an elongated member for an electrical stimulation system, the elongated member including a conductor electrically coupling a first contact to a second contact, the conductor including a plurality of spaced-apart closed switches disposed along a length of the conductor, according to the invention.
Figure 4B:
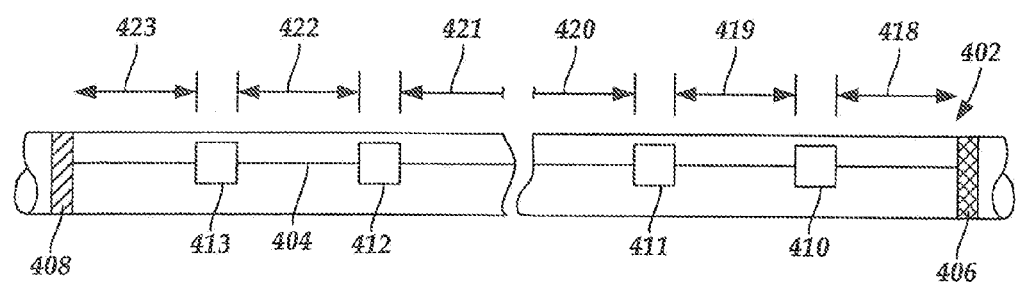
FIG. 4B is a schematic partial cross-sectional view of one embodiment of the elongated member shown in FIG. 4A, the elongated member including a conductor separated into individual segments by a plurality of spaced-apart open switches disposed along a length of the conductor, according to the invention.

FIGS. 4A-4B are schematic partial cross-sectional views of one embodiment of an elongated member 402. The elongated member 402 includes a conductor 404 electrically coupling a first contact 406 to a second contact 408. The conductor 404 includes one or more spaced-apart switches 410-413 disposed along a length of the conductor 404. In at least some embodiments, the switches 410-413 are configured and arranged to transition between an open position and a closed position, in FIG. 4A, the switches 410-413 are shown closed. In at least some embodiments, when the switches 410-413 are closed, electrical signals to and from the first contact 406 may transmit along the length of the conductor 404, through the switches 410-413, to or from the second contact 408, as shown by two-headed arrow 416 representing potential signal flow along the conductor 404. In FIG. 4B, the switches 410-413 are shown open. In at least some embodiments, when the switches 410-413 are open, the conductor 404 is separated into individual segments that are electrically isolated from one another, as shown by two-headed arrows 418-423 representing potential signal flow along the individual segments of the conductor 404.

In at least some embodiments, the elongated member 402 is a lead. In which case, the first contact 406 may be an electrode and the second contact 408 may be a terminal. In at least some embodiments, the elongated member 402 is a lead extension. In which case, the first contact 406 may be a conductive contact and the second contact 408 may be a terminal. In at least some embodiments, the elongated member 402 may include a plurality of conductors with one or more switches disposed on each conductor. In at least some other embodiments, the switches 410-413 may be disposed on other implantable devices, such as adapters, splitters, couplers, and the like.

The one or more switches 410-413 may be positioned at any suitable location along a length of the conductor 404. In at least some embodiments, at least one switch is disposed in proximity to the first contact 406. Any number of switches may be disposed along the length of the elongated member 402 including, for example, one, two, three, four, five, six seven, eight, nine, ten, twelve, fifteen, twenty, twenty-five or more switches. As will be recognized, other numbers of switches may be disposed along the length of the elongated member 402 as well.

Any suitable type of biocompatible, implantable switch may be used including, for example, electrical switches, magnetic switches, mechanical switches, and the like. Several examples of suitable switches include, nano-scale devices, magnetic devices, micro electro mechanical systems (MEMS), transistors, relays, reed switches, switches (or portions of switches) formed from shape memory materials (e.g., nitinol) which may change shape in response to exposure to changes in temperature, piezoelectric devices, inflatable devices (e.g., balloons, bladders, and the like), mechanical elements displaceable by exposure to magnetic fields, solid state electronics, bellows or spring elements, and the like or combinations thereof.

One or more of the switches may open or close in response to many different sources including, for example, receiving an electrical signal, exposure to a magnetic field, receiving a mechanical stimulus, and the like or combinations thereof.

In at least some embodiments, one or more of the switches open or close in response to an electrical signal. In at least some embodiments, the electric signal is delivered from a portion of the electrical stimulation system to the one or more switches via one or more control wires or a suitable wireless signal-transmission system. In at least some embodiments, the electric signal is delivered from one or more coupled implanted devices, such as adapters, splitters, couplers, and the like.

Figure 5:
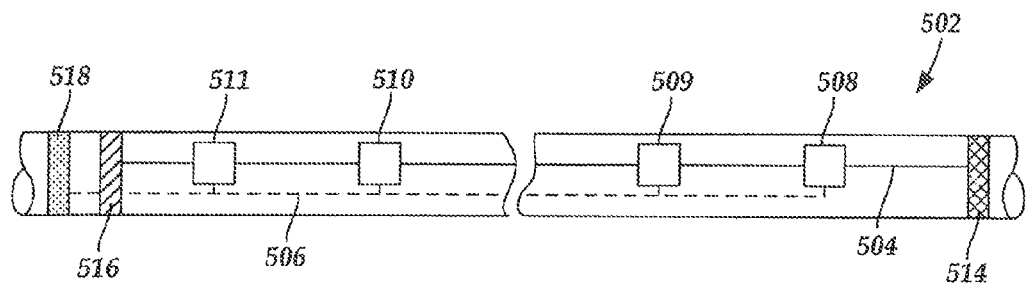
FIG. 5 is a schematic partial cross-sectional view of one embodiment of an elongated member that includes a conductor, the conductor including a plurality of spaced-apart switches disposed along a length of the conductor, the elongated member also including a control line electrically coupling each of the switches to a contact, according to the invention.

In at least some embodiments, the electrical signal is delivered from the control module (e.g., 102 in FIGS. 1-3A), or from a portion of the elongated member, via one or more control wires. FIG. 5 is a schematic partial cross-sectional view of one embodiment of an elongated member 502 that includes a conductor 504 and a control line 506. The conductor 504 includes a plurality of spaced-apart switches 508-511 disposed along a length of the conductor 504. The conductor 504 electrically couples a first contact 514 to a second contact 516. The control line 506 electrically couples each of the switches 508-511 to a third contact 518. In at least some embodiments, the control line 506 is configured and arranged to transmit an electrical signal to the switches 508-511. In at least some embodiments, the switches 508-511 open or close in response to receiving an electrical signal transmitted via the control line 506.

In at least some embodiments, the third contact 518 is separate from the second contact 516. In at least some embodiments, the third contact 518 is configured and arranged to couple electrically with the control module (e.g., 102 in FIGS. 1-3A). Thus, in at least some embodiments, the opening or closing of the switches 508-511 is controlled by an electrical signal transmitted from an electrically-coupled control module (e.g., 102 in FIGS. 1-3A), or from a portion of the elongated body 502.

In at least some embodiments, the electrical signals controlling the opening or closing of the switches may be delivered wirelessly. In at least some embodiments, one or more receivers may be used to receive wireless electrical signals. In at least some embodiments, one or more of the receivers may be disposed directly on the switches. In at least some embodiments, one or more of the receivers may be disposed on the control module. In some embodiments, one or more of the receivers may be disposed on other portions of the elongated body, such as along a wall of a lumen defined in the elongated body or along an outer surface of the elongated body, such as the lead body (106 in FIG. 1). Additionally, the electric signal may be delivered from one or more coupled implanted devices, such as adapters, splitters, couplers, and the like.

Figure 6:
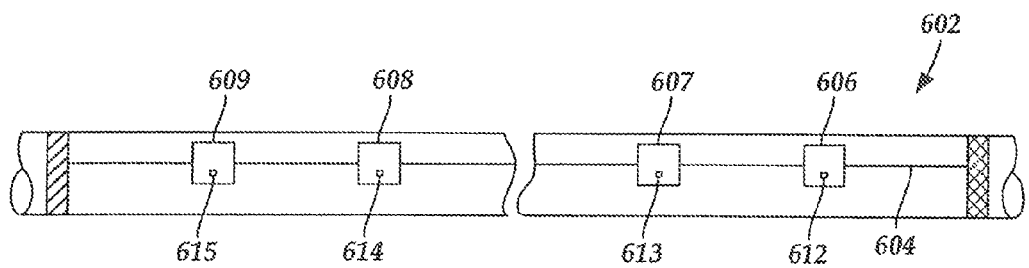
FIG. 6 is a schematic partial cross-sectional view of one embodiment of an elongated member that includes a conductor, the conductor including a plurality of spaced-apart switches disposed along a length of the conductor, the switches each including an actuator disposed on the switches, according to the invention.

FIG. 6 is a schematic partial cross-sectional view of one embodiment of an elongated body 602 that includes a conductor 604. The conductor 604 includes at least one spaced-apart switch 606-609 disposed along a length of the conductor 604. The switches 606-609 each include an actuator 612-615, respectively, disposed on the switches 606-609. In at least some embodiments, the actuators 612-615 may be configured and arranged to receive wireless electrical signals and respond to received electrical signals by sending a signal to the switches 606-609 to open or close. In at least some other embodiments, the actuators 612-615 may be configured and arranged to sense one or more stimuli, or a change in one or more conditions, and respond by sending a signal to the switches 606-609 to open or close. In at least some other embodiments, the actuators 612-615 may be configured and arranged to respond to a mechanical stimulus, either direct or indirect, by opening or closing the switches 606-609.

In at least some embodiments, electrical signals controlling the opening or closing of the switches may be transmitted from an external source (e.g., a remote control), in at least some embodiments, the electrical signals controlling the opening or closing of the switches may be delivered by an external instrument that is inserted into the patient and positioned in, or in close proximity to, the elongated member or the control module.

Figure 7:
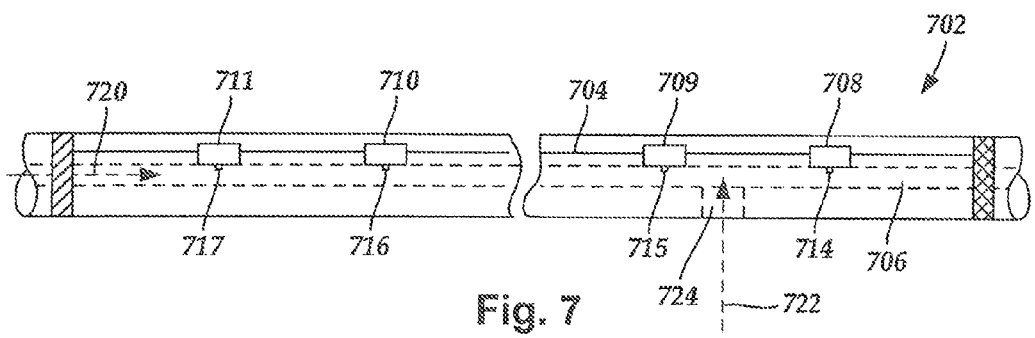
FIG. 7 is a schematic partial cross-sectional view of one embodiment of an elongated member that includes a conductor and a lumen, the conductor including a plurality of spaced-apart switches disposed along a length of the conductor, the switches each including an actuator abutting the lumen, according to the invention.

FIG. 7 is a schematic partial cross-sectional view of one embodiment of an elongated member 702 that includes a conductor 704 and defines at least one lumen 706. The conductor 704 includes at least one switch 708-711 with actuators 714-717, respectively, which abut the lumen 706. In at least some embodiments, an external instrument may be inserted into the lumen 706 and emit an electrical signal or provide some other type of stimulus (e.g., mechanical, magnetic, and the like), either through direct contact or remotely, which is received by the actuators 714-717, causing one or more of the switches 708-711 to open or close.

In at least some embodiments, the actuators 714-717 are disposed directly on the switches 708-711, respectively. In at least some embodiments, the actuators 714-717 are electrically coupled to the switches 708-711, respectfully, via one or more conductors. In at least some embodiments, the external instrument may be inserted into the lumen 706 from one end of the elongated member 702, as shown by arrow 720. In at least some embodiments, the external instrument may be inserted into the lumen 706 at some position along a length of the elongated member 702, as shown by arrow 722, in at least some embodiments, the external instrument may be inserted into the lumen 706 via an insertion port 724. In at least some embodiments, the external instrument may be inserted into the lumen 706 by extending the external instrument directly through an outer surface of the elongated member 702, such as the lead body (106 in FIG. 1).

In at least some embodiments, the electrical signal may be delivered by an external instrument that is inserted into a control module that is electrically coupled to the elongated member 702. For example, the electrically coupled control module may include a port which, when an external instrument is inserted into the port, delivers an electrical signal to one or more receivers disposed on the control module, which, in turn, cause the one or more actuators to transmit an electrical signal to the switches 606-609 to open or close.

In at least some embodiments, one or more sensors may be employed to sense one or more stimuli or conditions. For example, in at least some embodiments, the sensors may be configured and arranged to cause the switches to open or close in response to sensing radio frequency radiation with intensity above a threshold level. In at least some embodiments, the sensors may be configured and arranged to cause the switches to open or close in response to sensing a magnetic field with intensity above a threshold level. In at least some embodiments, the sensors may be configured and arranged to cause the switches to open or close in response to other stimuli with intensity above a threshold level including, for example, temperature, light, sound, carbon dioxide, pressure, and the like or combinations thereof.

In at least some embodiments, one or more of the sensors may be disposed directly on one or more switches (see e.g., FIG. 6). In at least some embodiments, one or more sensors may be disposed on the control module. In some embodiments, one or more sensors may be disposed on portions of the elongated member, such as along a wall of a lumen defined in the elongated member (see e.g. FIG. 7). In at least some embodiments, the sensors transmit signals to the switches via one or more control wires (see e.g. FIG. 5). In at least some embodiments, one or more sensors may be disposed on one or more coupled implanted devices, such as adapters, splitters, couplers, and the like.

In at least some embodiments, one or more of the switches open in response to exposure to a magnetic field. As discussed above, in at least some embodiments, sensors on the switches may be configured and arranged to cause the switches to open in response to sensing a magnetic field with intensity above a threshold level, in at least some embodiments, the threshold level may be set for a level which would typically be above the intensity of magnetic fields to which an individual may regularly be exposed, but that would be below a potentially harmful magnetic-field-intensity level. In at least some embodiments, the switches open in response to a magnetic field of at least 0.5 T. In at least some embodiments, the switches open in response to a magnetic field of at least 1.0 T. In at least some embodiments, the switches open in response to a magnetic field of at least 1.5 T. In at least some embodiments, the switches open in response to a magnetic field of at least 2.0 T.

As described above, in at least some embodiments, sensors on the switches may be configured and arranged to cause the switches to open or close in response to sensing environmental stimuli, such as a changes in temperature, light, sound, pressure, and the like. In at least some embodiments, environmental stimuli or conditions may be delivered by either an external source (e.g., a remote control) or an external instrument that is inserted into the electrical stimulation system on or around the actuators or the switches.

In at least some embodiments, one or more of the switches open or close in response to a mechanical stimulus. In at least some embodiments, a mechanical stimulus may cause one or more of the switches to open or close through either a direct or an indirect interface, in at least some embodiments, an external instrument may be inserted into the elongated member and used directly to open or close one or more of the switches or actuators. For example, as shown in FIG. 7, the external instrument may be inserted in the elongated member and used to apply pressure to one or more of the switches, thereby causing to one or more switches to open or close. In at lease some other embodiments, the external instrument inserted into the elongated member may be used to open or close one or more of the switches by physically interfacing with one or more switches or actuators. For example, the external instrument may be used to push, pull, flick, rotate, twist, bend, kink, or slide one or more features of one or more of the switches or actuators.

Additionally, in at least some embodiments the external instrument may be inserted into a portion of the electrical stimulation system and interface indirectly with the switches or actuators. For example, as shown in FIG. 7, a syringe may be inserted into the lumen of the elongated member and used to inject fluid which causes one or more of the switches to open or close by, for example, a change in pressure, or an inflation of a balloon, or a hydraulic effect, or the like or combinations thereof.

In at least some embodiments, one or more of the switches may be opened or closed by the application of stress to all, or a portion, of the electrical stimulation system. For example, in at least some embodiments, one or more of the switches may be opened or closed by twisting at least a portion of the electrical stimulation system. In at least some other embodiments, one or more of the switches may be opened or closed by stretching or compressing or pinching at least a portion of the electrical stimulation system. In at least some embodiments, one or more of the switches may be opened or closed by the application of tension (e.g., bending) or torque to at least one portion of the electrical stimulation system.

Figure 8:
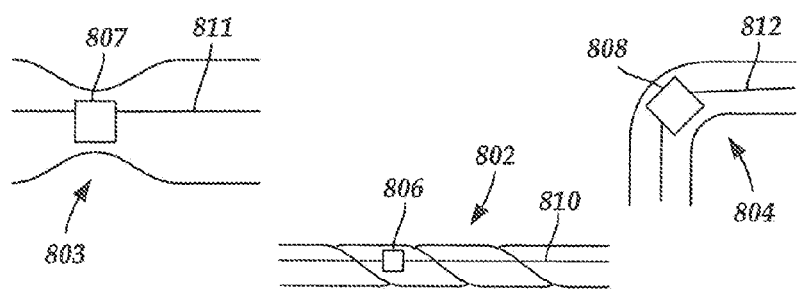
FIG. 8 is a schematic partial cross-sectional view of three embodiments of portions of three elongated members, each elongated member including a switch disposed on a conductor, a first elongated member opens or closes the switch in response to twisting, the second elongated member opens or closes the switch in response to squeezing, and the third elongated member opens or closes the switch in response to bending, according to the invention.
Figure 9:
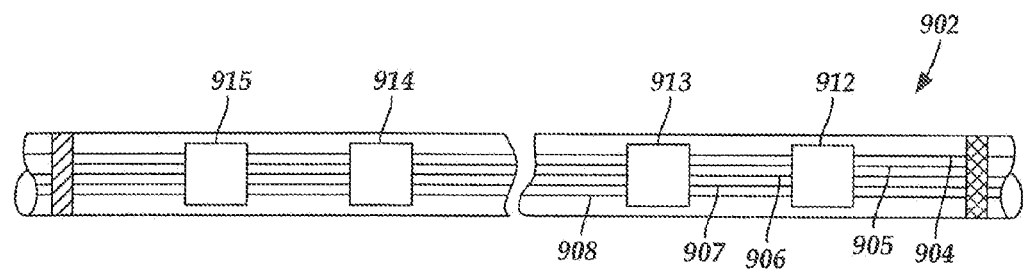
FIG. 9 is a schematic partial cross-sectional view of one embodiment of an elongated member that includes a plurality of conductors and a plurality of spaced-apart switches disposed along lengths of the conductors, the switches configured and arranged to electrically couple each of the conductors to at least one other of the conductors, according to the invention.

FIG. 8 is a schematic partial cross-sectional view of three embodiments of portions of three elongated members 802-804. Each elongated member 802-804 includes a switch 806-808, respectively, disposed along a length of a conductor 810-812, respectively. In FIG. 8, the switch 806 disposed in the elongated member 802 opens or closes in response to twisting a portion of the elongated member 802. The switch 807 disposed in the elongated member 803 opens or closes in response to squeezing a portion of the elongated member 803. The switch 808 disposed in the elongated member 804 opens or closes in response to bending a portion of the elongated member 804.

In at least some embodiments, continuous conductive loops may be formed in elongated member to eliminate or reduce the current generated in two or more conductors by RF irradiation, such as RF irradiation generated during MRI. In at least some embodiments, two or more of the switches may be used to electrically couple two or more of the conductors of the same elongated member to form one or more continuous conductive loons.

In at least some embodiments, each of the conductors in the elongated member is electrically isolated from other conductors in the elongated member when one or more switches are in closed positions, but two or more of the conductors may become electrically coupled together when one or more switches are transitioned to open positions. FIG. 8 is a schematic partial cross-sectional view of one embodiment of an elongated member 802 that includes a plurality of conductors 804-808 and a plurality of spaced-apart switches 812-815. Each of the spaced-apart switches 812-815 is electrically coupled to at least two of the conductors 804-808. In at least some embodiment, when the switches 812-815 are opened, the conductors 804-808 may form one or more continuous conductive loops within the elongated member 802.

Figure 10A:
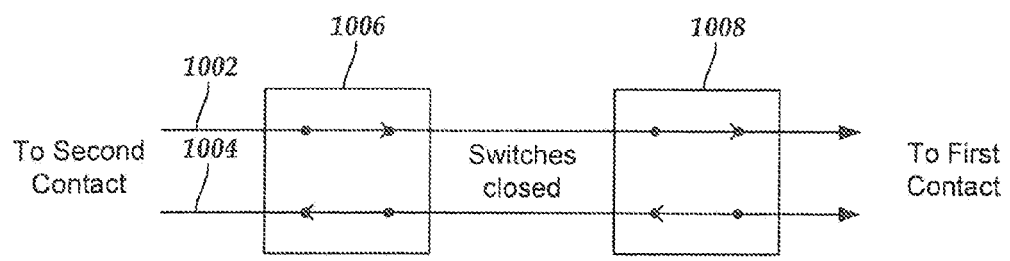
FIG. 10A is a schematic view of one embodiment of a portion of two conductors each coupled to two closed switches, the conductors transmitting signals from first contacts to second contacts, according to the invention.
Figure 10B:
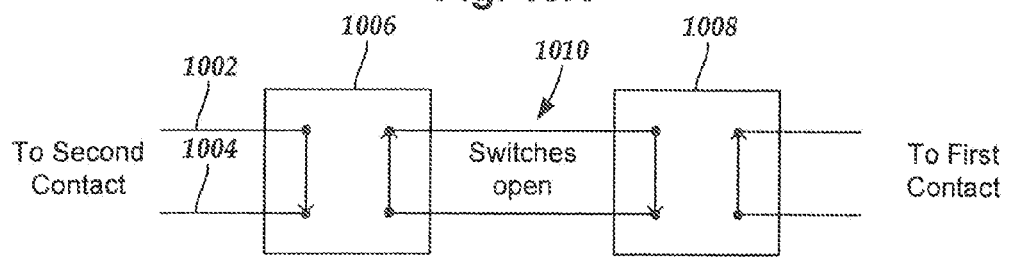
FIG. 10B is a schematic view of one embodiment of a portion of two conductors each coupled to two open switches, the conductors forming a continuous conductive loop, according to the invention.

FIGS. 10A and 10B are schematic views of one embodiment of a portion of two conductors 1002 and 1004 each coupled to two switches 1006 and 1008. In FIG. 10A, the switches 1006 and 1008 are closed. Consequently, the conductors 1002 and 1004 are isolated from one another and signals may be transmitted along conductors 1002 and 1004 from a second conductor (408 in FIG. 4A) to a first conductor (406 in FIG. 4A). In FIG. 10B, the switches 1006 and 1008 are open. Consequently, the conductors 1002 and 1004 may form one or more continuous conductor loops 1010 and signals may be transmitted from a second conductor (408 in FIG. 4A) may not reach a first conductor (406 in FIG. 4A), it will be understood that additional conductors and additional switches may be electrically coupled to switches to form many different possible continuous conductor loops along different conductors and switches.

In at least some embodiments, the elongated member includes at least one switch with a closed position and an open position that electronically isolates a coupled conductor into a plurality of individual segments electrically isolated from each other and at least one switch with a closed position and an open position that electrically couples two or more conductors together to form continuous conductor loops.

In at least some embodiments, conductors of an elongated member are configured and arranged so that the switches are closed during standard operation and the one or more switches are opened in response to a specific potentially-adverse stimuli or condition, as discussed above. After the potentially-adverse stimuli or condition is removed or subsides, the one or more switches may need to be reset to a closed position.

In at least some embodiments, the one or more switches may automatically return to a closed position when the stimulus or condition which opened the one or more switches is removed or subsides, in at least some embodiments, the one or more switches may reset to a closed position after another exposure to another stimulus or condition above the critical threshold. In at least some embodiments, the exposure may be to either to the same stimulus or condition which caused the one or more switches to open, or to a different stimulus or condition. In at least some embodiments, the one or more switches may reset by manually transmitting a signal from an external device pressing a RESET button on a remote control). In at least some embodiments, in the absence of another resetting event, the one or more switches may automatically reset to a closed position after a given period of time.

Figure 11:
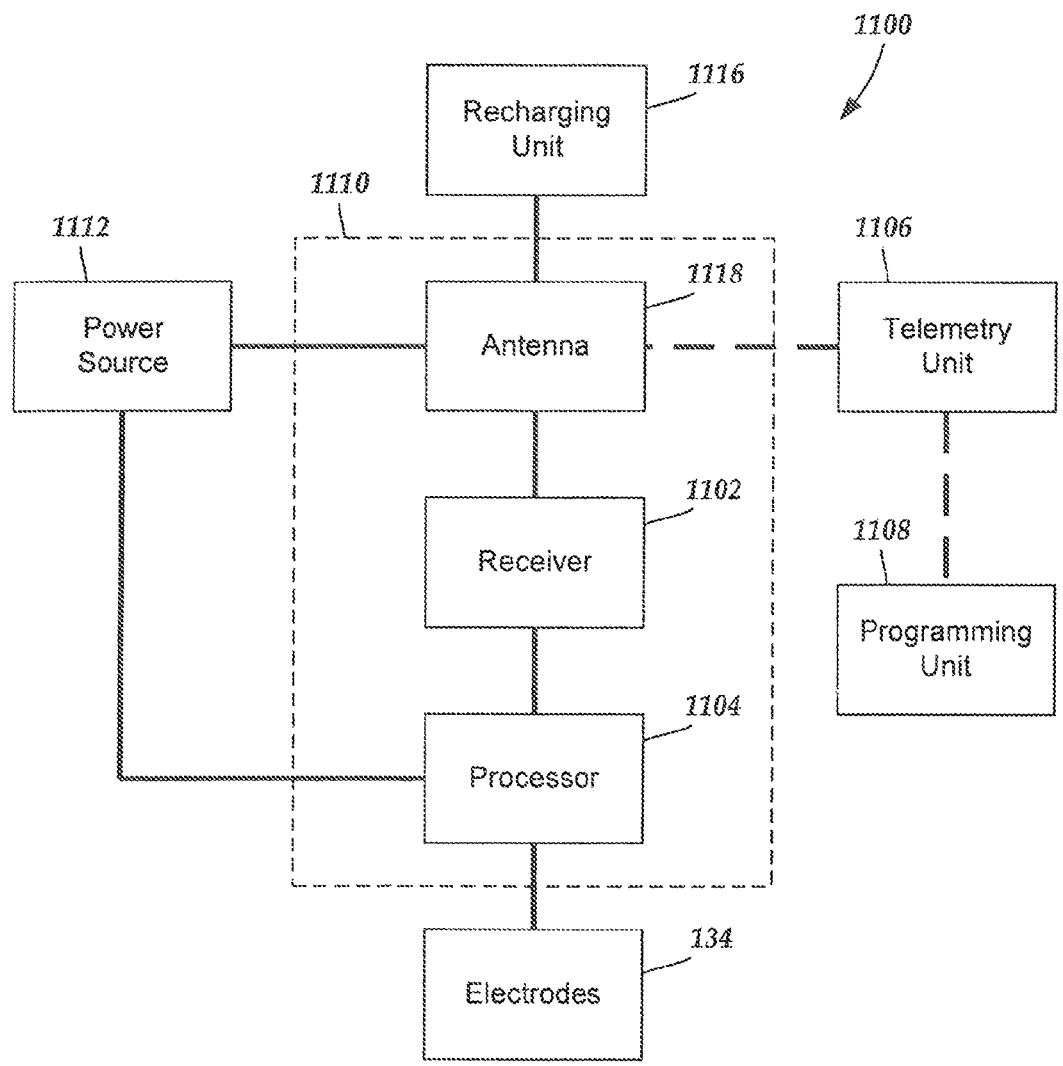
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes, in some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by U.S. Letters Patent:

1. A method of neural stimulation, the method comprising:
   implanting a lead in a patient, the lead comprising a lead body having a proximal end and a distal end, a plurality of electrodes disposed on the distal end of the lead body, a plurality of terminals disposed on the proximal end of the lead body, and a plurality of conductors extending along the lead body, wherein each of the plurality of conductors electrically couples at least one of the electrodes to at least one of the terminals, wherein at least one of the conductors comprises a plurality of switches disposed along a length of the conductor and configured and arranged to separate the conductor into a plurality of individual segments when the plurality of switches are opened;
   providing signals to the electrodes to produce neural stimulation of tissue in the patient; and opening the plurality of switches when an intensity from at least one of a magnetic field or radio-frequency radiation meets a threshold criterion.

2. The method of claim 1, wherein opening the plurality of switches comprises providing an electrical signal to the plurality of switches to open the plurality of switches.

3. The method of claim 2, wherein providing an electrical signal comprises providing an electrical signal to the plurality of switches along at least one control line disposed in the lead to open the plurality of switches.

4. The method of claim 2, wherein providing an electrical signal comprises providing an electrical signal wirelessly to the plurality of switches to open the plurality of switches.

5. The method of claim 1, wherein opening the plurality of switches comprises mechanically opening the plurality of switches.

6. The method of claim 5, wherein mechanically opening the plurality of switches comprises twisting at least a portion of the lead to open the plurality of switches.

7. The method of claim 5, wherein mechanically opening the plurality of switches comprises squeezing at least a portion of the lead to open the plurality of switches.

8. The method of claim 5, wherein mechanically opening the plurality of switches comprises bending at least a portion of the lead to open the plurality of switches.

9. The method of claim 5, wherein mechanically opening the plurality of switches comprises applying pressure to the plurality of switches to open the plurality of switches.

10. The method of claim 9, wherein applying pressure to the plurality of switches comprises applying pressure to the plurality of switches through a lumen extending along the lead to open the plurality of switches.

11. The method of claim 10, wherein applying pressure to the plurality of switches through a lumen comprises inserting an external instrument into the lumen to apply pressure to the plurality of switches.

12. The method of claim 10, wherein applying pressure to the plurality of switches through a lumen comprises injecting a fluid into the lumen to apply pressure to the plurality of switches.

13. The method of claim 1, wherein each of the conductors comprises the plurality of switches disposed along a length of the conductor and configured and arranged to separate the conductor into a plurality of individual segments when the plurality of switches are opened.

14. The method of claim 1, wherein opening the plurality of switches comprises magnetically opening the plurality of switches.

15. The method of claim 1, further comprising coupling a control module to the lead and implanting the control module.

16. The method of claim 15, wherein coupling a control module to the lead comprising coupling the lead to a lead extension and coupling the lead extension to the control module.

17. The method of claim 15, further comprising monitoring an intensity from at least one of a magnetic field or radio frequency radiation using a sensor disposed in the control module.

18. The method of claim 17, wherein opening the plurality of switches comprises opening the plurality of switches in response to the sensor determining that the intensity from at least one of the magnetic field or the radio-frequency radiation meets a threshold criterion.

19. The method of claim 1, wherein opening the plurality of switches comprises, for each of the plurality of switches when the switch is opened, coupling portions of two of the plurality of conductors together to form, in combination with at least one other of the plurality of switches, a continuous conductor loop comprising the switch and the coupled portions of the two of the plurality of conductors.

20. The method of claim 1, wherein each of the plurality of switches is part of each of two or more of the plurality of conductors.

* * * * *